United States Patent
Vandekerckove

(10) Patent No.: US 9,533,017 B2
(45) Date of Patent: Jan. 3, 2017

(54) *SACCHAROMYCES CEREVISIAE* YEAST FOR PREVENTING AND/OR TREATING VAGINAL MYCOSES

(71) Applicant: LESAFFRE ET COMPAGNIE, Paris (FR)

(72) Inventor: Pascal Vandekerckove, Villeneuve D'ascq (FR)

(73) Assignee: LESAFFRE ET COMPAGNIE, Paris (FR)

( * ) Notice: Subject to any disclaimer, the term of this patent is extended or adjusted under 35 U.S.C. 154(b) by 0 days.

(21) Appl. No.: 14/414,259

(22) PCT Filed: Jul. 9, 2013

(86) PCT No.: PCT/FR2013/051643
§ 371 (c)(1),
(2) Date: Jan. 12, 2015

(87) PCT Pub. No.: WO2014/009656
PCT Pub. Date: Jan. 16, 2014

(65) Prior Publication Data
US 2015/0182568 A1 Jul. 2, 2015

(30) Foreign Application Priority Data
Jul. 13, 2012 (FR) ...................................... 12 56799

(51) Int. Cl.
*A61K 36/06* (2006.01)
*A61K 36/064* (2006.01)
*A61K 45/06* (2006.01)

(52) U.S. Cl.
CPC ............. *A61K 36/064* (2013.01); *A61K 45/06* (2013.01)

(58) Field of Classification Search
None
See application file for complete search history.

(56) References Cited

U.S. PATENT DOCUMENTS

| 8,460,649 B2* | 6/2013 | Pujos | A01N 63/04 424/93.51 |
| 8,476,058 B2* | 7/2013 | Simon | A23L 1/3016 424/93.51 |
| 2007/0059298 A1 | 3/2007 | Volkmann | |
| 2010/0303778 A1* | 12/2010 | Simon | A23L 1/3016 424/93.51 |
| 2011/0301030 A1* | 12/2011 | Pujos | A01N 63/04 504/101 |
| 2015/0182568 A1* | 7/2015 | Vandekerckove | A61K 45/06 424/195.16 |

FOREIGN PATENT DOCUMENTS

| BR | 0 002 018 | 1/2002 |
| BR | 0002018 | 1/2002 |
| WO | 2009/103884 | 8/2009 |
| WO | WO 2009/103884 | 8/2009 |

OTHER PUBLICATIONS

Jawhara et al, PLoS ONE, Jul. 2012, 7/7:e40648. 15 pages (www.plosone.org).*
Etienne-Mesmin et al, Applied and Environmental Microbiology, Feb. 2011, p. 1127-1131 vol. 77, No. 3.*
McCullough et al, Journal of Clinical Microbiology, Feb. 1998, p. 557-562 vol. 36, No. 2.*
International Search Report dated Sep. 26, 2013, which issued during prosecution of International Application No. PCT/FR2013/051643.
Papaemmanouil, et al. "Prevalence and susceptibility of causing vaginitis in Greek women" Anaerobe 17 (6):298-299, Apr. 2011.
International Search Report issued for International application No. PCT/FR2013/051643.
Papaemmanouil V et al: Prevalence andsusceptibility of causing vaginitis inGreek women Anaerobe, London, GB, vol. 17, No. 6, Apr. 13, 2011.

* cited by examiner

*Primary Examiner* — Nita M Minnfield
(74) *Attorney, Agent, or Firm* — Vedder Price P.C.; Thomas J. Kowalski; Deborah L. Lu

(57) ABSTRACT

The present invention relates to the *Saccharomyces Cerevisiae* strain deposited with the French National Collection of Micro-organism Cultures under number CNCM I-3856, or a *Saccharomyces cerevisiae* yeast obtained by culturing said strain for the use thereof in the prevention and/or treatment of vaginal mycoses, and in particular vaginal candidiasis.

20 Claims, 3 Drawing Sheets

SACCHAROMYCES CEREVISIAE YEAST FOR PREVENTING AND/OR TREATING VAGINAL MYCOSES

RELATED PATENT APPLICATIONS

Figure 1:
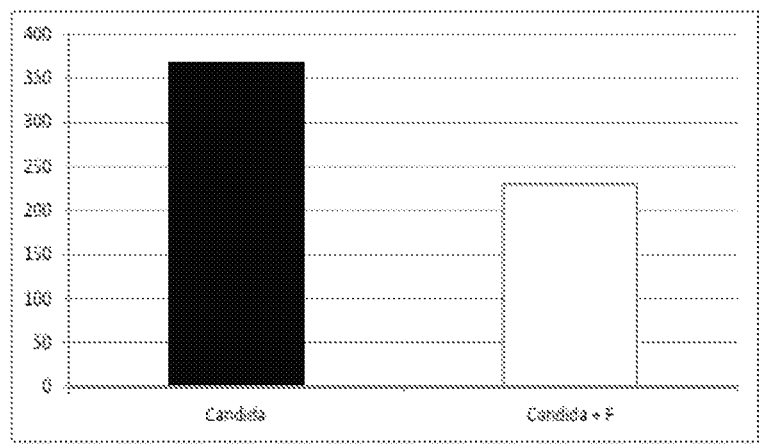

The present application is filed pursuant to 35 U.S.C. 371 as an U.S. National Phase Application of International Patent Application No. PCT/FR2013/051643, which was filed on Jul. 9, 2013, claiming the benefit of priority to French Patent Application No. FR 12 56799 filed on Jul. 13, 2012. The content of each of the aforementioned Patent Applications is incorporated herein by reference in its entirety.

The present invention relates to a novel therapeutic use of a *Saccharomyces cerevisiae* yeast, namely use for preventing and/or treating vaginal mycoses.

Vaginal or vulvovaginal mycoses are mainly caused by infection with pathogenic fungi, most often *Candida albicans*, in a woman's intimate area.

Vaginal mycoses are now regarded as an important public health problem and constitute the second commonest cause of vaginal infection after bacterial vaginitis.

It is estimated that 75% of women develop a vaginal mycosis at some time. About 50% of them have at least 2 or 3 episodes of vaginal mycoses during their life. 10 to 20% of women suffer from recurring vaginal mycoses with on average 4 episodes per year.

In the year 2000 it was estimated in the United States that the medico-economic costs of treating this disorder were of the order of a billion dollars per year.

The antimycotic treatments usually employed to date are based on the use of therapeutic molecules, principally azole derivatives such as for example fluconazole, ketoconazole, econazole, miconazole or clotrimazole, generally administered in the form of cream or as a pessary. In certain cases, treatment by the oral route is used as a supplement to topical treatment.

However, one of the major problems with this type of treatment is that, in repetitive vaginal mycoses, the pathogenic fungus, in particular *Candida albicans*, may develop resistance to the existing antimycotic treatments.

Another problem in using azole derivatives for treating mycoses is the sensation of irritation and burning at the level of the vulva.

Recent publications have shown that the use of probiotics (*Lactobacillus rhamnosus* GR-1 & *Lactobacillus reuteri* RC14) combined with the molecule fluconazole gave an increase in efficacy of fluconazole in the treatment of mycoses (Martinez et al., Letters in Applied Microbiology, 2009, (48)269-274).

It should be pointed out that the probiotic effect of a given strain, whether it is a bacterial strain or a yeast strain, is specific to this strain, and not the genus and species in question.

Moreover, it is known that although vaginal mycoses are predominantly caused by *Candida albicans*, cases of infections caused by *Saccharomyces cerevisiae* have been described (Savini et al., Mycopathologia, 2008, 166: 47-50).

One of the aims of the present invention is therefore to propose new medicinal products or food supplements with a health effect intended for preventing and/or treating vaginal mycosis.

Another aim of the invention is to propose new medicinal products or food supplements with a health effect intended for treating mycosis that do not have the aforementioned drawbacks connected with using azole derivatives (development of resistance, side-effects such as irritation, burning, etc.), while displaying efficacy at least comparable to the existing treatments.

The present inventors found, surprisingly, that the use of the *Saccharomyces cerevisiae* strain deposited on Oct. 17, 2007 at the CNCM (National Collection of Cultures of Microorganisms, 25, rue du Docteur Roux, 75724 Paris cedex 15, France) under number I-3856 allowed these aims to be achieved.

The Deposit with the COLLECTION NATIONALE DE CULTURES DE MICROORGANISMES (CNCM), under deposit accession number CNCM I-3856 was made pursuant to the terms of the Budapest Treaty. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

Thus, the invention relates to the *Saccharomyces cerevisiae* strain deposited by the applicant at the CNCM under number I-3856 for use thereof in the prevention and/or treatment of vaginal mycoses, and more particularly vaginal candidoses.

The *Saccharomyces cerevisiae* strain deposited under number I-3856 was previously described by the applicant in document WO 2009/103884. This strain was more particularly described for use in the prevention and/or treatment of intestinal diseases, disorders or complaints.

However, the behavior of the pathogenic fungi and of the probiotics with respect to the intestinal mucosa is not transposable to that adopted with respect to the vaginal mucosa, the environment of these mucosae notably being different.

As far as the applicant knows, this is the first time that a strain of *Saccharomyces cerevisiae* has been described as having an effect in the prevention and/or treatment of vaginal mycoses.

The expression "yeast strain" denotes a relatively homogeneous population of yeast cells.

A yeast strain is obtained by isolating a clone, a clone being a population of cells obtained from a single yeast cell.

According to another embodiment, the present invention relates to *Saccharomyces cerevisiae* yeast obtained by culturing the *Saccharomyces cerevisiae* strain deposited at the CNCM under number I-3856, for use thereof in the prevention and/or treatment of vaginal mycoses, and more particularly of vaginal candidoses.

The yeast according to the invention is obtained by culturing the strain number I-3856 in a culture medium, for example as described in the reference work "Yeast Technology", 2nd edition, 1991, G. Reed and T. W. Nagodawithana, published by Van Nostrand Reinhold, ISBN 0-442-31892-8.

The yeast according to the invention may be obtained by a process on an industrial scale that comprises the following two steps:
culturing a yeast strain in a culture medium in several stages, firstly in semi-anaerobiosis, then in aerobiosis,
separating the yeast thus produced from its culture medium, by centrifugation, to obtain a liquid yeast cream containing between 12 and 25% of dry matter, or even a higher content of dry matter, especially if the yeast cream is mixed with osmolytic products.

In the present invention, the terms "yeast obtained by culturing the *Saccharomyces cerevisiae* strain deposited at the CNCM under number I-3856", "yeast obtained by culturing the strain I-3856" and "yeast Sc I-3856" will be used indifferently, as these three terms have the same meaning as given above.

According to yet another embodiment, the invention relates to a derivative of the yeast obtained by culturing the *Saccharomyces cerevisiae* strain deposited at the CNCM under number I-3856, for use thereof in the prevention and/or treatment of vaginal mycoses, in particular vaginal candidoses, said derivative being selected from the cell wall of said yeast, the cell wall glucans of said yeast, the cell wall mannoproteins of said yeast or mixtures thereof.

The yeast wall denotes broadly both the wall and the plasma membrane of the yeast.

Conventionally, the yeast wall is obtained by a process comprising a step of autolysis of the yeast followed by a step of separating the soluble fraction from the insoluble fraction, the insoluble fraction isolated corresponding to the yeast wall, which may then be dried.

The present invention relates in particular to a wall of the Sc I-3856 yeast, for use thereof in the prevention and/or treatment of vaginal mycoses, at a daily dose from 1 mg to 10 g, and preferably from 100 mg to 1 g.

The present invention also relates to cell wall glucans of the Sc I-3856 yeast, for use thereof in the prevention and/or treatment of vaginal mycoses, at a daily dose from 0.25 mg to 2.5 g, and preferably from 25 mg to 250 mg.

The present invention relates in particular to cell wall mannoproteins of the Sc I-3856 yeast, for use thereof in the prevention and/or treatment of vaginal mycoses, at a daily dose from 0.1 mg to 1 g, and preferably from 10 mg to 100 mg.

"Vaginal mycosis" means any infection in the vaginal area caused by fungi.

The term "vaginal" is used broadly and the terms "vaginal" and "vulvovaginal" are synonyms here.

"Vaginal candidosis" means a particular type of vaginal mycosis due to fungi of the genus *Candida*, for example those selected from the group comprising *Candida albicans, Candida tropicalis, Candida pseudotropicalis, Candida krusei, Candida glabrata* and mixtures thereof.

Vaginal candidosis is also called candidal vaginitis.

The present invention thus also relates to a strain as defined above, a yeast as defined above or a derivative as defined above, for use thereof in the prevention and/or treatment of vaginal candidoses, for example candidoses due to fungi selected from the group comprising *Candida albicans, Candida tropicalis, Candida pseudotropicalis, Candida krusei, Candida glabrata* and mixtures thereof.

The Sc I-3856 yeast may be used prophylactically in women having a predisposition and/or sensitivity to vaginal mycoses, notably vaginal candidoses, or therapeutically, for example during episodes of infection.

Without wishing to be bound to a theory, the present inventors are of the opinion that the administration of a yeast obtained by culturing the I-3856 strain makes it possible to inhibit the multiplication of *Candida* in the vagina, notably by reducing the adherence of *Candida* to the vaginal mucosa. Moreover, the cell wall polysaccharide structures, especially glucans and mannans, would play a role in this mechanism of action.

According to an advantageous embodiment of the invention, the Sc I-3856 yeast used is live.

The live yeast is then for example in the form of a fresh yeast or in the form of a dry yeast.

The present invention notably relates to the Sc I-3856 yeast in the form of dry yeast or fresh yeast, for use thereof in the prevention and/or treatment of vaginal mycoses, for example at a daily dose from $1·10^7$ to $1·10^{11}$ CFU, and preferably from $1·10^9$ to $1·10^{10}$ CFU.

A fresh yeast is characterized by a high water content.

A fresh yeast is selected for example from a compressed yeast and a liquid yeast.

A liquid yeast according to the invention, also called "liquid yeast cream", is an aqueous suspension comprising from 12% to 50% of yeast dry matter, more generally from 12% to 22% of yeast dry matter.

A compressed yeast according to the invention is obtained by:
  filtration of a liquid yeast cream, generally on a rotary vacuum filter, to obtain a dewatered fresh yeast containing from 26% to 37% of dry matter,
  mixing said dewatered fresh yeast and extrusion.

A compressed yeast comprises from 26% to 37% of yeast dry matter.

Compressed yeast may or may not be crumbled.

Among the dry yeasts, we may for example mention active dry yeast, instant dry yeast, and frozen yeast with intermediate moisture content.

An advantage of a dry yeast is its long shelf life.

An active dry yeast or an instant active dry yeast according to the invention comprises a level of yeast dry matter above 90%, preferably a level of dry matter in the range from 92% to 96%.

Active dry yeast is obtained by dewatering compressed yeast or liquid yeast by the combined action of heat (at low temperature) and mechanical activity, which make it possible to transform a pasty product (compressed yeast or liquid yeast) into a dry product, in the form of spherules.

For example, active dry yeast is obtained by extrusion and fluidized-bed drying of a compressed yeast or of a liquid yeast.

Active dry yeast is in the form of spherules generally with a diameter from 0.1 μm to 2.5 mm.

Instant dry yeast is obtained by dewatering compressed yeast or liquid yeast by the action of a gradient of hot air, which makes it possible to transform a pasty product (compressed yeast or liquid yeast) into fine dry "noodles". For it to remain stable, the instant dry yeast must then be packaged in the absence of oxygen.

Frozen dry yeast with intermediate moisture content comprises for example from 70% to 85% of yeast dry matter.

in a preferred embodiment, the Sc I-3856 yeast used according to the invention in the prevention and/or treatment of vaginal mycoses is in the form of active dry yeast or in the form of instant dry yeast.

According to another advantageous embodiment of the invention, the Sc I-3856 yeast used according to the invention in the prevention and/or treatment of vaginal mycoses is in the form of dead yeast, also called deactivated yeast.

A dead yeast is a yeast whose metabolism has stopped irreversibly.

A dead yeast may be obtained by techniques well known by a person skilled in the art, such as a heat treatment of the yeast, a treatment consisting of subjecting the yeast to several cycles of successive freezing and thawing, a treatment by irradiation, a treatment by spraying or a combination of these treatments.

The present invention also relates to the Sc I-3856 yeast in the form of dead yeast, for use thereof in the prevention and/or treatment of vaginal mycoses, at a daily dose from 1 mg to 10 g, and preferably from 100 mg to 1 g.

The present invention also relates to a strain as defined above, a yeast as defined above or a derivative as defined above, for use thereof in the prevention and/or treatment of vaginal mycoses, said strain, said yeast or said derivative being administered by the oral route or by the vaginal route, preferably by the vaginal route.

The invention also relates to a composition comprising the Sc I-3856 yeast and/or a derivative of said yeast, for use in the prevention and/or treatment of vaginal mycoses.

The composition according to the invention may be a pharmaceutical composition, a food supplement with a health effect or a food composition.

The invention also relates to a composition comprising the Sc I-3856 yeast and/or a derivative of said yeast, and optionally at least one pharmaceutically acceptable excipient for use in the prevention and/or treatment of vaginal mycoses.

The vaginal mycoses are as defined above.

The composition according to the invention is intended for administration by the oral route or the vaginal route, the vaginal route being preferred.

As an example of a composition that is in a form suitable for the oral route, we may mention a tablet, a soft capsule, a hard capsule, a sachet, a powder, a cream, a syrup or an ampule.

As an example of a composition that is in a form suitable for the vaginal route, we may mention a pessary, a soft capsule, a hard capsule, a cream or a tablet.

The excipients used in the composition according to the invention are excipients used conventionally that are suitable for preparing oral or vaginal dosage forms.

The daily dose depends both on the type of mycoses, the method of administration (oral route or vaginal route) and the type of treatment—therapeutic or prophylactic.

According to a particular embodiment of the invention, the composition comprises the Sc I-3856 yeast in the form of dead yeast, for daily use in an amount from 1 mg to 10 g, and preferably from 100 mg to 1 g.

According to another embodiment of the invention, the composition comprises the Sc I-3856 yeast in dry or fresh form, for daily use in an amount from $1 \cdot 10^7$ to $1 \cdot 10^{11}$ CFU, and preferably from $1 \cdot 10^9$ to $1 \cdot 10^{10}$ CFU.

According to another embodiment of the invention, the composition comprises a cell wall of the Sc I-3856 yeast, for daily use in an amount from 1 mg to 10 g, and preferably from 100 mg to 1 g.

According to another embodiment of the invention, the composition comprises cell wall glucans of the Sc I-3856 yeast, for daily use in an amount from 0.25 mg to 2.5 g, and preferably from 25 mg to 250 mg.

According to another embodiment of the invention, the composition comprises cell wall mannoproteins of the Sc I-3856 yeast, for daily use in an amount from 0.1 mg to 1 g, and preferably from 10 mg to 100 mg.

The effective daily dose may be administered in one, two or three administrations.

The present invention also relates to a pharmaceutical composition comprising the Sc I-3856 yeast and/or the derivative of the Sc I-3856 yeast in combination with another active principle and optionally a pharmaceutically acceptable excipient, for use in the prevention and/or treatment of vaginal mycoses.

The active principle used in combination with the Sc I-3856 yeast may be an active principle having a soothing, anti-irritant, analgesic, antalgic, anti-inflammatory, wound-healing, antifungal, antimycosic and/or antimycotic activity.

When the pharmaceutical composition comprises the Sc I-3856 yeast and/or the derivative of the Sc I-3856 yeast in combination with an active principle having an antifungal activity, said active principle having an antifungal activity does not have any effect on *Saccharomyces cerevisiae*.

The terms "antifungal", "antimycosic" and "antimycotic" are synonyms here.

Figure 2:
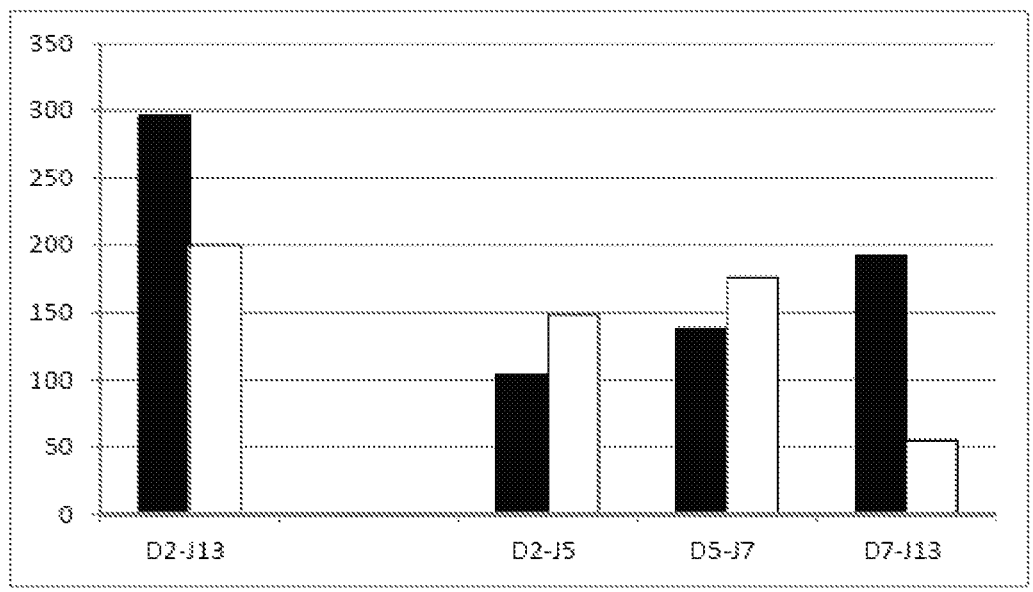
Figure 3:
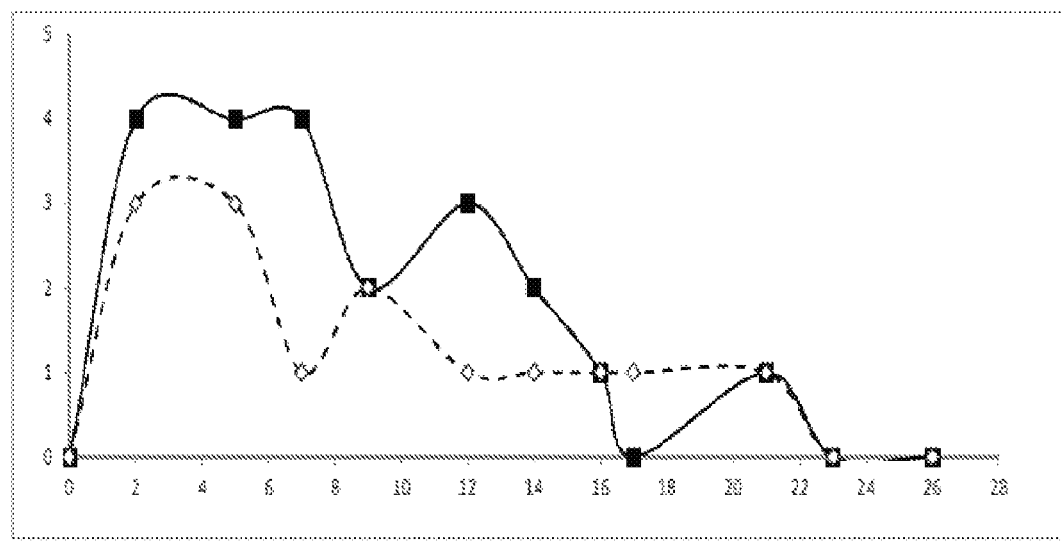
Figure 4:
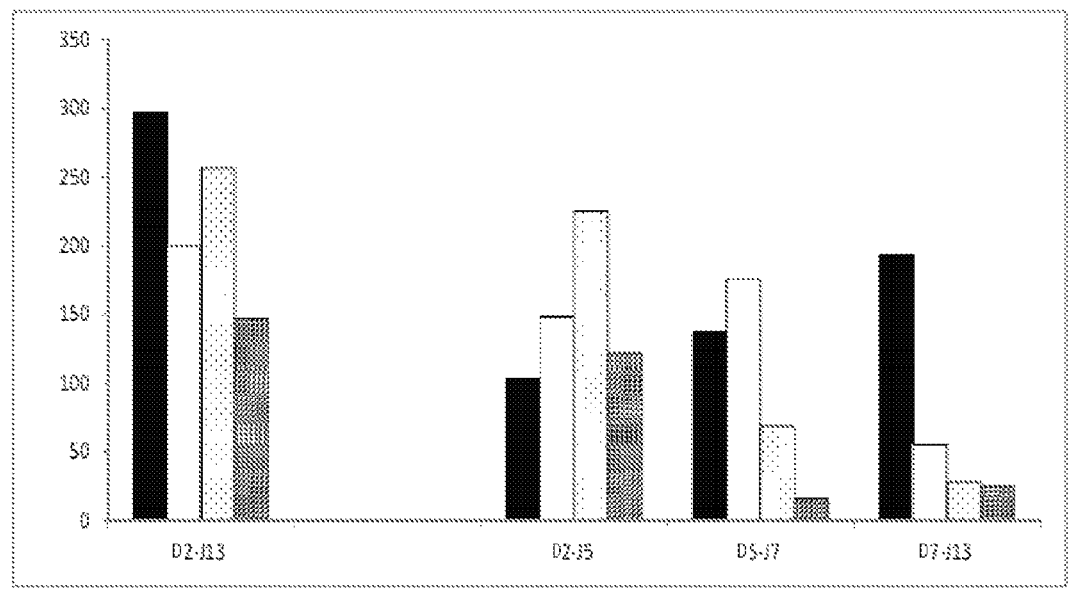
Figure 5:
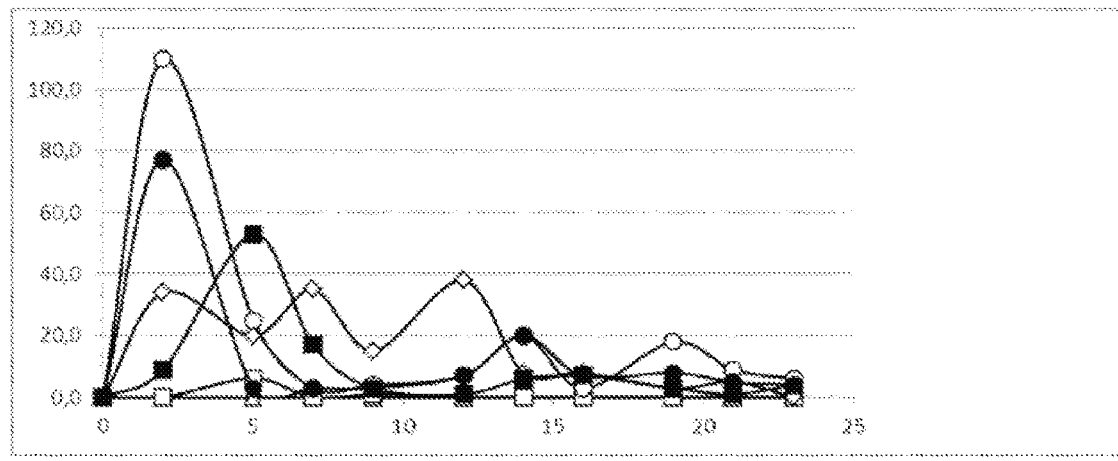

The present invention will now be illustrated based on the examples and figures that are given below for purposes of illustration, which are not in any way limiting, in which:

FIG. 1 is a histogram showing the AUC (Area Under Curve) values representative of the number of viable cells of *Candida albicans* found at the level of the vaginal mucosa of rats treated with fluconazole (white) or not treated with fluconazole (black) in the first thirteen days following infection with *Candida albicans*, FIG. 2 is a histogram showing the AUC (Area Under Curve) values representative of the number of viable cells of *Candida albicans* found at the level of the vaginal mucosa of rats treated with fluconazole (white) or not treated with fluconazole (black) between days D2-D13, D2-D5, D5-D7 and D7-D13 following infection with *Candida albicans*, FIG. 3 shows a semiquantitative evaluation of the antigens of mannoside structure characteristic of *Candida albicans* as a function of time (in days), present in rats treated with fluconazole (white diamonds) or untreated (black squares) after infection with *Candida albicans*, FIG. 4 is a histogram showing the AUC values for the untreated rats (black), the rats treated with fluconazole (white) or the rats treated with the Sc I-3856 yeast as prophylactic treatment (dashes) or therapeutic treatment (hatched), between days D2-D13, D2-D5, D5-D7 and D7-D13 following infection with *Candida albicans*, FIG. 5 shows the number of viable cells of *Candida albicans* (in CFU) found in the wash liquids of the untreated rats (white diamonds) or rats treated with fluconazole (black squares), or with the Sc I-3856 yeast as prophylactic treatment (white circles) or therapeutic treatment (black circles), after infection with *Candida albicans*, and in the uninfected control rats (white triangles) and the uninfected control rats treated with the Sc I-3856 yeast (white squares).

Figure 6:
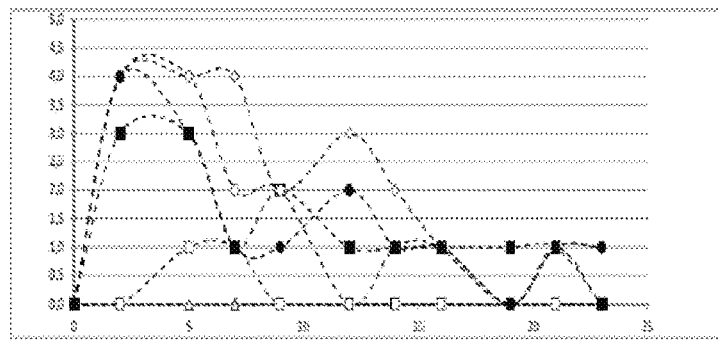

FIG. 6 shows a semiquantitative evaluation of the antigens of mannoside structure characteristic of *Candida albicans* as a function of time (in days), present respectively in the untreated rats (white diamonds) or rats treated with fluconazole (black squares), or with the Sc I-3856 yeast as prophylactic treatment (white circles) or therapeutic treatment (black circles) after infection with *Candida albicans*, in the uninfected control rats (white triangles) and the uninfected control rats treated with the Sc I-3856 yeast (white squares).

EXAMPLE

Definition of A Model of Vaginal Infection Induced by *Candida Albicans* in Female Rats and Demonstration of the Effect of the Sc I-3856 Yeast in this Model The model developed below made it possible to demonstrate that the administration of the Sc I-3856 yeast in female rats makes it possible to prevent and/or treat vaginal mycoses caused by an infection induced by *Candida albicans* (*C. albicans*).

Material and Methods

The animal experiments are carried out in establishments approved by the Institut Pasteur in Lille, according to the European directives on animal experiments.

The cell count is obtained by the method of counting by colony. The values are expressed in Colony Forming Unit (CFU).

The animals are housed 3 per cage with free access to standard feed for rats as well as to tap water.

Ovariectomized female rats (Sprague-Dawley) aged from 3 to 5 weeks are purchased from Janvier Laboratoires, France. They are maintained under pseudo-estrus by a subcutaneous injection of estradiol benzoate (Sigma, estradiol benzoate resuspended in sesame oil; 0.5 mg/animal) every other day (i.e. three times per week) up to the end of the experiment.

A week after the first injection of estradiol inducing pseudo-estrus, the female rats are infected with C. albicans. Infection with C. albicans corresponds to a single intravaginal administration of the C. albicans strain at a concentration of $10^7$ CFU.

The female rats are distributed in 6 different groups as indicated below.

| Group tested | Single infection with C. albicans | Sc I-3856 yeast | Volume | Route of application | Number of animals per group |
|---|---|---|---|---|---|
| Vehicle | 0 | 0 | 100 µl | intravaginal administration | 7 |
| C. albicans | $10^7$ CFU | 0 | 100 µl | intravaginal administration | 7 |
| Sc I-3856 yeast | 0 | $10^7$ CFU | 100 µl | intravaginal administration | 7 |
| C. albicans + Sc I-3856 yeast Prophylactic | $10^7$ CFU | $10^7$ CFU | 100 µl | intravaginal administration | 7 |
| C. albicans + Sc I-3856 yeast Therapeutic | $10^7$ CFU | $10^7$ CFU | 100 µl | intravaginal administration | 7 |
| Candida + Fluconazole (50 µg) | $10^7$ CFU | 0 | 100 µl | intravaginal administration | 7 |

The Sc I-3856 yeast tested is in the form of an active dry yeast.

Fluconazole is the reference antifungal, used as positive control as it is usually employed for treating vaginal candidosis.

Fluconazole is administered by the intravaginal route at a dose of 50 µg per rat, respectively 1 h, 24 h and 48 h after infection with C. albicans.

Prophylactic Treatment with the Sc I-3856 Yeast

The Sc I-3856 yeast suspended in PBS buffer is administered at a dose of $10^7$ CFU per rat by intravaginal administration, respectively 48 h, 24 h and 1 h before infection with C. albicans.

The Sc I-3856 yeast is then administered every 8 days up to the end of the experiment.

Therapeutic Treatment with the Sc I-3856 Yeast

The Sc I-3856 yeast suspended in PBS buffer is administered at a dose of $10^7$ CFU per rat by intravaginal administration, respectively 1 h, 24 h and 48 h after infection with C. albicans.

The yeast ScI-3856 is then administered every 8 days up to the end of the experiment.

Evaluation of Growth of the Colony of C. albicans

The number of colonies of C. albicans adhering to the vaginal mucosa is evaluated every two days after infection with Candida albicans and up to the end of the experiment (3 weeks later) by taking a cervico-uterine smear (with a calibrated loop) and by spreading on Chrom-Agar plates (a growth medium specific and selective for Candida), 5 vaginal samples being combined.

The viable colonies of Candida albicans are counted after two days of culture at 30° C. on a selective medium (Chrom-Agar plates, BD).

Cytologic Evaluation of Inflammation

The smears are prepared from a cervical sample and from washes.

Preparations of cells in a thin layer on slides are prepared from combined washes in each group of rats (washes from 5 rats) using a cytocentrifuge (Cytospin®). The slides are fixed using an aerosol cytologic fixative (Cytoral®).

A vaginal sample is taken from 2 rats per group, 10 days after infection with C. albicans.

Conventional May Grunwaid Giemsa staining is carried out for evaluating the level of inflammation in the groups of rats that received C. albicans alone or combined with the treatment with the Sc I-3856 yeast.

Cytologic studies are also undertaken and Papanicolaou staining is carried out in order to evaluate hormonal colpocytology. The study is conducted on a cervico-uterine smear.

Immunohistochemical staining is also performed on vaginal sections and cervico-uterine smears using antibodies directed against C. albicans (5B2) or lectin of Galanthus nivalis (GNL) for the Sc I-3856 yeast.

Biological Analyses

The pH of the combined vaginal washes is evaluated every two days using a pH strip.

Detection of an antigen of C. albicans is useful for diagnosing vaginal candidosis. The antigen comprises a highly immunogenic mannoside structure present in the cell wall of C. albicans. The antigen with mannoside structure is the main antigen present in vaginal infection, it therefore constitutes a useful biomarker for diagnosing invasive candidosis.

A first possibility for detecting the presence of the antigen with mannoside structure consists of using the ELISA immuno-enzyme technique (Platelia Candida Ag assay, Bio-Rad).

The level of antigen of C. albicans is evaluated in the combined vaginal washes, diluted to 1/10 with a standard heat treatment, according to the manufacturers' instructions. The quantity of antigens detected is expressed in picograms per ml.

Another possibility for detecting the presence of the antigen with mannoside structure consists of using ICT strips (Candi Vagi, SR2B). "ICT" is based on capture of the antigen contained in the vaginal secretions using a mouse immunoglobulin IgM directed against the antigen with mannoside structure. The monoclonal antibody recognizes the epitopes of the antigen with mannoside structure for a wide range of Candida species. The monoclonal antibody is conjugated to particles or in a mobile phase and is also applied on a nitrocellulose strip as capture antibody. The ICT stick is put in the suspension of vaginal sample and the samples move by capillary action through the block containing the "MAb-gold" conjugate (Mab for monoclonal antibody). The analysis is performed as described in the publication Marot-Leblond et al., Journal of Clinical Microbiology, 2009.

The level of inflammation is evaluated by measuring the level of calprotectin (an enzyme released by the neutrophils) in the vaginal samples and is quantified using a kit validated for quantifying human calprotectin in the stool (Labodia kit).

The statistical analyses are performed using the Permutation Test for two independent samples. The statistics are calculated using the StatXact software (Cytel Inc, Cambridge, Mass., USA). The differences are considered to be statistically significant if the p value is below 0.05.

Results and Discussion

With Fluconazole Control

Cervico-Uterine Smears Corresponding to the Presence of Viable C. albicans in the Vaginal Mucosa of the Rats Table 1 below shows the mean growth of the colonies of C. albicans on Chrom-Agar plates in each group of rats (5 rats per group).

|  | Duration, days | | | | | | | | | |
| --- | --- | --- | --- | --- | --- | --- | --- | --- | --- | --- |
|  | 2 | 5 | 7 | 10 | 13 | 15 | 17 | 20 | 23 | 25 |
| Control | 0 ± 0 | 0 ± 0 | 0 ± 0 | 0 ± 0 | 0 ± 0 | 0 ± 0 | 0 ± 0 | 0 ± 0 | 0 ± 0 | 0 ± 0 |
| C. albicans | 14.75 ± 5.12 | 16.25 ± 1.43 | 35 ± 9.5 | 49.71 ± 13.51 | 48.4 ± 15.53 | 20.8 ± 9.55 | 26 ± 6.98 | 16 ± 5.37 | 15.6 ± 11.8 | 10.6 ± 4.01 |
| C. albicans + fluconazole | 5.25 ± 1.37 | 25 ± 6.5 | 42 ± 5.18 | 17 ± 5.29 | 7 ± 2.5 | 34.45 ± 5.26 | 24.4 ± 9.7 | 8.8 ± 4.33 | 11.8 ± 7.55 | 11.6 ± 4.97 |

It may therefore be concluded that:

administration of C. albicans leads to a progressive infection of the vaginal mucosa starting on day 2 with a maximum intensity on day 12 followed by a phase of spontaneous elimination; day 12 is regarded as the optimal time for C. albicans infection in this model;

administration of fluconazole leads to absence of infection with C. albicans on day 12 with presence of a small number of C. albicans in the vaginal mucosa observed on day 7.

Another way of expressing the results is to calculate the area under the curve (AUC) between day 2 and day 12, which represents a quantitative marker of the presence of viable C. albicans in the vaginal mucosa of rats receiving or not receiving fluconazole.

Treatment with fluconazole causes a 36% decrease in the number of viable C. albicans in the first 12 days after infection.

Thus, C. albicans leads to a progressive vaginal infection with peak intensity on day 12. Antimycotic treatment with the fungicide fluconazole leads to a 36% decrease in infection of the vaginal mucosa and prevention of vaginal candidosis on day 12. These results are presented in FIG. 1.

Liquid Washes Corresponding to Elimination of C. albicans

Table 2 below shows the number of C. albicans CFUs determined from the washes.

|  | Duration in days | | | | | | | | | |
| --- | --- | --- | --- | --- | --- | --- | --- | --- | --- | --- |
|  | 2 | 5 | 7 | 10 | 13 | 15 | 17 | 20 | 23 | 25 |
| Control | 0 | 0 | 0 | 0 | 0 | 0 | 0 | 0 | 0 | 0 |
| C. albicans | 34 | 20 | 35 | 15 | 38 | 8 | 8 | 3 | 5 | 0 |
| C. albicans + fluco | 9 | 53 | 17 | 3 | 1 | 6 | 7 | 3 | 1 | 4 |

It may therefore be concluded that the viable C. albicans (CFU) are regularly and constantly released in the vaginal washes between day 2 and 16 (about 30 CFU).

The treatment with fluconazole increases the release of Candida over the course of the first 8 days after infection with peak intensity on day 5.

Another way of expressing the results is to calculate the area under curve (AUC) between day 2 and day 12, which is a quantitative marker of the elimination of viable C. albicans in the vaginal wash of rats receiving or not receiving fluconazole.

In other words, the AUC value is representative of the number of viable C. albicans found in the vaginal mucosa of the rats.

The antimycostatic activity of fluconazole causes a 20% decrease in elimination of viable C. albicans between days 2 and 12 in the treated rats relative to the untreated rats (see FIG. 2).

Treatment with fluconazole increases the elimination of viable C. albicans by 45% in the first week after infection.

If the experiment is split into various steps, it is observed that fluconazole firstly induces a rapid, high release of C. albicans in the wash (Days 2-5 and 5-7) relative to the untreated rats (see FIG. 2).

In fact, treatment with fluconazole induces release of C. albicans that is twice as great (73%) as the natural release (34.6%) observed in the infected but untreated rats (34.6%) between days 2 and 5, indicating that the effect of fluconazole is a first or early effect.

The antigen with mannoside structure is quantified using non-commercial strips in combined washes from 5 rats.

The quantity of antigens with mannoside structure is less in the rats treated with fluconazole than in the untreated rats. The largest difference in the quantity of antigen is observed on day 13 in the infected rats treated with fluconazole compared to the untreated infected rats (see FIG. 3).

Cytologic Analysis of Vaginal Washes

Slides are prepared from the combined vaginal washes and MGG staining is carried out in order to evaluate the appearance of the vaginal epithelial cells, the presence of bacteria and yeasts and the presence of proinflammatory cells.

On day 2, the control samples are characterized by the presence of normal vaginal epithelial cells, without the presence of inflammatory cells. The main difference in the rats infected with C. albicans is the presence of a large number of polynuclear neutrophils (PNN) and some eosinophils indicating the inflammatory state induced by infection with C. albicans.

Treatment with fluconazole prevents inflammatory infiltration. The presence of a few C. albicans is observed, probably corresponding to increasing release of the yeast by the treatment.

On day 12 after infection with C. albicans, similar observations are obtained in the control group relative to the observations on day D2. In the group infected with C. albicans, the presence of a large number of macrophages and of some neutrophils is observed, which indicates that C. albicans is well established and induces inflammation. In the rats treated with fluconazole, not one C. albicans cell is observed and only a few macrophages and neutrophils are present.

Conclusion:

The model of vaginal infection with *C. albicans* and the various methods for analyzing this model are validated.

The therapeutic effect of a treatment can be analyzed optimally on day D12 after infection with *C. albicans*.

Efficacy of the Sc I-3856 Yeast

The preventive and/or curative therapeutic effects of the Sc I-3856 yeast are evaluated in the model of vaginal candidosis elaborated above and are compared with the effect of fluconazole administered therapeutically (1 h, 24 h and 48 h after infection with *C. albicans*). For prophylaxis, the Sc I-3856 yeast is administered 48 h, 24 h and 1 h before infection with *Candida* and once every 7 days after infection with *C. albicans*.

The number of *C. albicans* (in CFU) is determined from cervico-uterine smears and washes as described above.

The results are presented in Table 3 below.

| | Duration in days | | | | | | | | | |
|---|---|---|---|---|---|---|---|---|---|---|
| | 2 | 5 | 7 | 10 | 13 | 15 | 17 | 20 | 23 | 25 |
| Control | 0 ± 0 | 0 ± 0 | 0 ± 0 | 0 ± 0 | 0 ± 0 | 0 ± 0 | 0 ± 0 | 0 ± 0 | 0 ± 0 | 0 ± 0 |
| *C. albicans* | 14.7 ± 5.12 | 16.25 ± 1.43 | 35 ± 9.5 | 49.71 ± 13.51 | 48.4 ± 15.53 | 20.8 ± 9.55 | 26 ± 6.98 | 16 ± 5.31 | 15.6 ± 11.8 | 10.6 ± 4.01 |
| *C. albicans* + fluco | 5.25 ± 1.37 | 25 ± 6.5 | 42 ± 5.18 | 17 ± 5.29 | 7 ± 2.5 | 34.45 ± 5.26 | 24.4 ± 9.7 | 8.8 ± 4.33 | 11.8 ± 7.55 | 11.6 ± 4.97 |
| *C. albicans* + Yeast Sc I-3856 Prophylactic | 29.25 ± 12.68 | 19.5 ± 3 | 53.42 ± 7.22 | 14.42 ± 3.38 | 17.8 ± 5.8 | 21.2 ± 3.54 | 12.2 ± 2.08 | 15.4 ± 5.04 | 22.8 ± 7.41 | 18 ± 3.76 |
| *C. albicans* + Yeast Sc I-3855 Therapeutic | 18 ± 4 | 24.75 ± 8.375 | 36.71 ± 10.57 | 30.14 ± 11.20 | 33.6 ± 13.92 | 20.8 ± 9.55 | 13.6 ± 7.76 | 11.6 ± 2.72 | 9.2 ± 2.65 | 8.4 ± 1.36 |

Regarding analysis of the cervico-uterine smears and the growing number of cells of *C. albicans* on the Chrom-Agar plates, on day D13 we observe a marked decrease in CFUs in the infected rats treated with the Sc I-3856 yeast in a prophylactic treatment relative to the untreated infected rats, with 17.8 (±5.85) vs 48.4 (±15.53) respectively, which corresponds to a 63% decrease in infections on day D13.

Thus, treating the rats with the Sc I-3856 yeast reduces the number of viable *C. albicans* in the vaginal mucosa by 30% relative to the untreated animal.

Table 4 below shows the AUC values from day D2 to day D13.

| Treatment | AUC values (D2 to D13) | Difference |
|---|---|---|
| *C. albicans* | 372.43 | |
| *C. albicans* + Fluconazole | 236.875 | 135.555 |
| *C. albicans* + Sc I-3856 yeast Prophylactic | 296.68 | 75.75 |
| *C. albicans* + Sc I-3856 yeast Therapeutic | 320.945 | 51.485 |

It may be concluded that the prophylactic treatments with the Sc I-3856 yeast have an effect similar to fluconazole, reducing the AUC values by 20% and 36% respectively relative to the untreated rats.

Table 5 below gives results for growth of *C. albicans* CFUs based on washes.

| | Duration in days | | | | | | | | | |
|---|---|---|---|---|---|---|---|---|---|---|
| | 2 | 5 | 7 | 10 | 13 | 15 | 17 | 20 | 23 | 25 |
| control | 0 | 0 | 0 | 0 | 0 | 0 | 0 | 0 | 0 | 0 |
| *C. albicans* | 34 | 20 | 35 | 15 | 38 | 8 | 8 | 3 | 5 | 0 |
| *C. albicans* + fluco | 9 | 53 | 17 | 3 | 1 | 6 | 7 | 3 | 1 | 4 |
| *C. albicans* + Sc-I3856 Prophylactic | 110 | 25 | 3 | 4 | 7 | 20 | 3 | 18 | 9 | 6 |
| *C. albicans* + ScI-3856 Therapeutic | 77 | 3 | 3 | 3 | 7 | 20 | 7 | 8 | 5 | 4 |

As described above in the model of vaginal candidosis, the results may be separated into two phases, namely a first step on days D2-D5 corresponding to a marked release of *C. albicans* and a second step on day D13.

Analysis of the results on day D13 after infection with *C. albicans* shows a marked decrease in the number of viable *C. albicans* present in the washes with fluconazole and the Sc I-3856 yeast (prophylactic and therapeutic treatment) relative to infected rats without treatment (1 for fluconazole and 7 for the Sc I-3856 yeast against 38 in the untreated infected rats).

Administration of the Sc I-3856 yeast (as prophylactic or therapeutic treatment) is characterized by rapid release of the viable *C. albicans* in the 5 days after infection, suggesting that the Sc I-3856 yeast may limit adherence/invasion of *C. albicans* in the vaginal mucosa. Elimination of *C. albicans* is quicker with the Sc I-3856 yeast than with fluconazole.

Table 6 below shows the AUC values (=quantitative marker of the presence of *C. albicans* in the vaginal mucosa of the rats) from day D2 to day D13.

| Treatment | AUC values (D 2-13) |
|---|---|
| *C. albicans* | 290.5 |
| *C. albicans* + fluconazole | 199 |
| *C. albicans* + Sc I-3856 yeast Prophylactic | 257.6 |
| *C. albicans* + Sc I-3856 yeast Therapeutic | 150 |

Analysis of the AUC values shows a greater effect of the Sc I-3856 yeast when it is administered in therapeutic treatment after infection with *C. albicans*, halving the AUC value, corresponding to a smaller number of *C. albicans* present in the washes, with 150 versus 290.5 respectively.

The Sc I-3856 yeast administered as therapeutic treatment has a greater effect on infection with *C. albicans* than that induced by fluconazole, with 150 versus 199 respectively.

If the different periods of the experiment are separated into days D2-D5, D5-D7 and D7-D13 respectively, in the first phase of treatment (D2-D5) it is observed that administration of the Sc I-3856 yeast as prophylactic treatment induces a marked release of *C. albicans* (see FIG. 4).

It is therefore highly likely that the Sc I-3856 yeast, when administered as prophylactic treatment, inhibits adhesion of *C. albicans* to the vaginal mucosa. Then, only a few *C. albicans* grow (from day D5 to day D13) (see FIG. 4).

Calculation of the percentage of CFUs of *C. albicans* that grow in the first phase of the experiment just after infection with *C. albicans* (D2-D5) shows that 88% of the CFUs are detected in prophylactic treatment with the Sc I-3856 yeast, 82% of the CFUs are detected in therapeutic treatment with the Sc I-3856 yeast and 73% with the treatment with fluconazole.

These results indicate that treatment with the Sc I-3856 yeast has an efficacy that is higher or similar to that obtained with fluconazole for preventing adherence of *C. albicans*.

The antigens of *C. albicans* with mannoside structure are quantified in the wash liquids (FIG. 6). A good correlation is observed between the number of *C. albicans* cells (obtained from vaginal washes) that grow on Chrom-Agar plates and the levels of antigens measured in the same washes (FIG. 5).

All the *C. albicans* cells, viable and dead, are measured using the same method of immunodetection, in contrast to the conventional method with selective medium allowing multiplication of the viable cells of *C. albicans*.

For cytologic investigation of the vaginal washes, slides are prepared from the combined vaginal washes and MGG staining is carried out.

The appearance of the vaginal epithelial cells, the presence of bacteria and yeasts and the presence of proinflammatory cells are evaluated by observation (results not shown).

On day D2, the control group is characterized by the presence of normal vaginal epithelial cells, without presence of inflammatory cells. The main difference in the rats infected with *C. albicans* is the presence of a large number of polynuclear neutrophils (PNN) and some eosinophils indicating the inflammatory state induced by infection with *C. albicans*.

Treatment with fluconazole prevents inflammatory infiltration. The presence of some *C. albicans* is observed, probably corresponding to increased release of *C. albicans* by the treatment.

On day D12 after infection with *C. albicans*, similar observations are obtained in the control group relative to day D2. In the rats infected with *C. albicans*, the presence of a large number of macrophages and of some neutrophils is observed, indicating that the *C. albicans* are well established and induce inflammation. In the rats treated with fluconazole, no *C. albicans* is observed, but some macrophages and neutrophils are observed. In the rats treated with fluconazole, presence of *C. albicans* is observed, but no immune cell is found (results not shown).

In the rats treated prophylactically with the Sc I-3856 yeast, macrophages, neutrophils and eosinophils are observed two days after infection with *C. albicans*, but at lower density than that observed in the rats infected with *C. albicans* (results not shown).

In the rats treated therapeutically with the Sc I-3856 yeast, no macrophage and no eosinophil is observed, but an increased number of neutrophils is present, as was observed in the rats infected with *C. albicans*.

The presence of *C. albicans* is observed in the rats infected with *C. albicans* and treated using fluconazole or using the Sc I-3856 yeast (as prophylactic or therapeutic treatment), but is not observed in the rats infected with *C. albicans* and not treated, which demonstrates the efficacy of treatment inducing release or prevention of adhesion of *C. albicans* to the vaginal mucosa.

On day D12 after infection with *C. albicans*, similar observations are obtained in the control group relative to the observations on day D2. In the rats infected with *C. albicans*, the presence of a large number of macrophages and of some neutrophils is observed, indicating that the *C. albicans* are well established and induce inflammation. In the rats treated with fluconazole, no *C. albicans* is observed, but some macrophages and neutrophils are observed.

In the rats treated prophylactically with the Sc I-3856 yeast, no macrophage is observed, but the presence of neutrophils is observed.

In the rats treated therapeutically with the Sc I-3856 yeast, the presence of macrophages and neutrophils is observed. However, compared to the rats infected with *C. albicans*, fewer macrophages are observed, which indicates a decrease in inflammation due to administration of the Sc I-3856 yeast (results not shown).

CONCLUSION

The applicant has developed a new model of vaginal candidosis in female rats. The maximum intensity of vaginal infection is observed 12 to 13 days after administration of *Candida albicans*. The positive control using antimycotic treatment with fluconazole makes it possible to prevent infection with *Candida albicans* completely, 12 days after said administration, and increases the release of *Candida albicans* in the vaginal lumen particularly during the first six days of infection.

Prophylactic treatment using the Sc I-3856 yeast also shows a strong therapeutic effect allowing vaginal infection to be reduced 12 to 13 days after administration of *Candida albicans* in more than 60% of the treated rats in comparison with the untreated rats. This prophylactic effect is very probably due to rapid release of *Candida albicans* in the vaginal lumen, which occurs during the first 4 days following infection with *Candida albicans*.

The therapeutic treatment is also effective though with slightly lower efficacy relative to that of the prophylactic treatment.

Compared to the treatment using fluconazole, the prophylactic treatment using the Sc I-3856 yeast leads to a quicker release of *Candida albicans* in the vaginal lumen of the rats with vaginal candidosis.

There is a large decrease in viable *Candida albicans* in the vaginal mucosa of the rats after 12 to 13 days in the two groups of rats treated with fluconazole or with the Sc I-3856 yeast respectively, but it is slightly greater with the treatment with fluconazole. This slightly greater decrease is probably due to the antimycotic effect of the fluconazole molecule.

The invention claimed is:

1. A method for the prevention and/or the treatment of vaginal mycoses, comprising administering an effective dose of the *Saccharomyces cerevisiae* strain deposited on Oct. 17, 2007 at the CNCM under registration number CNCM I-3856 to a subject in need thereof.

2. A method for the prevention and/or the treatment of vaginal mycoses, comprising administering an effective dose of yeast obtained by culturing the *Saccharomyces cerevisiae* strain deposited on Oct. 17, 2007 at the CNCM under registration number CNCM I-3856 to a subject in need thereof.

3. The method as claimed in claim 2, wherein the yeast is in the form of fresh yeast or in the form of dry yeast.

4. The method as claimed in claim 3, wherein the yeast is in the form of active dry yeast or instant dry yeast.

5. The method as claimed in claim 2, wherein the yeast is in the form of dead yeast.

6. A method for the prevention and/or the treatment of vaginal mycoses, comprising administering an effective dose of a derivative of the yeast obtained by culturing the *Saccharomyces cerevisiae* strain deposited on Oct. 17, 2007 at the CNCM under registration number CNCM I-3856 to a subject in need thereof, said derivative being selected from the cell wall of said yeast, the cell wall glucans of said yeast, the cell wall mannoproteins of said yeast or mixtures thereof.

7. The method as claimed in claim 1, wherein the vaginal mycoses are of vaginal candidoses.

8. The method as claimed in claim 7, wherein the vaginal candidoses are due to fungi selected from the group comprising *Candida albicans, Candida tropicalis, Candida pseudotropicalis, Candida krusei, Candida glabrata* and mixtures thereof.

9. A method for the prevention and/or the treatment of vaginal mycoses comprising administering an effective dose of a composition comprising a yeast obtained by culturing the *Saccharomyces cerevisiae* strain deposited on Oct. 17, 2007 at the CNCM under registration number CNCM I-3856 and/or a derivative of said yeast to a subject in need thereof, wherein the composition optionally comprises at least one pharmaceutically acceptable excipient.

10. The method as claimed in claim 9, wherein the composition is administered by the oral route or by the vaginal route.

11. The method as claimed in claim 9, wherein said yeast is in the form of dead yeast, for daily use in an amount from 1 mg to 10 g.

12. The method as claimed in claim 9, wherein said yeast is in the form of dry yeast or fresh yeast, for daily use in an amount from $1.10^7$ to $1.10^{11}$ CFU.

13. The method as claimed in claim 9, wherein said yeast and/or said derivative is in combination with another active principle.

14. The method as claimed in claim 13, wherein the other active principle is selected from the group of active principles having a soothing, anti-irritant, analgesic, anti-inflammatory, wound-healing, antifungal, and/or antimycotic activity.

15. The method as claimed in claim 2, wherein the vaginal mycoses are vaginal candidoses.

16. The method as claimed in claim 6, wherein the vaginal mycoses are vaginal candidoses.

17. The method as claimed in claim 15, wherein the vaginal candidoses are due to fungi selected from the group comprising *Candida albicans, Candida tropicalis, Candida pseudotropicalis, Candida krusei, Candida glabrata* and mixtures thereof.

18. The method as claimed in claim 16, wherein the vaginal candidoses due to fungi selected from the group comprising *Candida albicans, Candida tropicalis, Candida pseudotropicalis, Candida krusei, Candida glabrata* and mixtures thereof.

19. The method as claimed in claim 11, wherein said yeast is for daily use in an amount from 100 mg to 1 g.

20. The method as claimed in claim 12, wherein said yeast is for daily use in an amount from $1.10^9$ to $1.10^{10}$ CFU.

* * * * *